(12) United States Patent
Castellucci et al.

(10) Patent No.: US 9,879,184 B2
(45) Date of Patent: Jan. 30, 2018

(54) PREPARATION PROCESS OF A FLAME RETARDANT COMPOSITION MADE FROM BROMINATED BISMUTH AND/OR ANTIMONY COMPOUNDS COMPLEXED WITH MELAMINE AND COMPOSITION OBTAINED THEREBY

(71) Applicant: Sichim Alfa S.r.l., Ravenna (IT)

(72) Inventors: Anita Castellucci, Ferrara (IT); Alessandro Bottoni, Ferrara (IT)

(73) Assignee: SICHIM ALFA S.R.L., Ravenna (IT)

( * ) Notice: Subject to any disclaimer, the term of this patent is extended or adjusted under 35 U.S.C. 154(b) by 0 days.

(21) Appl. No.: 15/517,355

(22) PCT Filed: Jul. 28, 2015

(86) PCT No.: PCT/IB2015/055691
§ 371 (c)(1),
(2) Date: Apr. 6, 2017

(87) PCT Pub. No.: WO2016/067126
PCT Pub. Date: May 6, 2016

(65) Prior Publication Data
US 2017/0292076 A1    Oct. 12, 2017

(30) Foreign Application Priority Data
Oct. 27, 2014   (EP) .................................... 14425136

(51) Int. Cl.
*C09K 21/10*   (2006.01)
*C08K 5/3492*   (2006.01)
*C07D 251/70*   (2006.01)

(52) U.S. Cl.
CPC ............ *C09K 21/10* (2013.01); *C07D 251/70* (2013.01); *C08K 5/34922* (2013.01)

(58) Field of Classification Search
CPC ........................... C09K 21/10; C08K 5/34922
See application file for complete search history.

(56) References Cited

U.S. PATENT DOCUMENTS 4,798,857 A  *  1/1989  Bertelli ................... C07F 9/902
                                                              252/609
5,166,235 A     11/1992  Bertelli et al.

FOREIGN PATENT DOCUMENTS

WO       2005019330 A2     3/2005

OTHER PUBLICATIONS

Bertelli, et al., "Fire Retardant Systems Based on Melamine Hydrobromide: Part I—Fire Retardant Behaviour", Polymer Degradation and Stability, 1987, vol. 18, No. 3, pp. 225-236.
Costa et al., "Thermal Degradation and Fire Retardancy of Antimony and Bismuth Trihalides-Melamine Complexes", Polymer Degradation and Stability, 1991, vol. 34, pp. 55-73.
PCT Written Opinion and International Search Report, Application No. PCT/IB2015/055691, dated Nov. 16, 2015.

* cited by examiner

*Primary Examiner* — Peter F Godenschwager
(74) *Attorney, Agent, or Firm* — MacMillan, Sobanski & Todd, LLC

(57) ABSTRACT

The invention relates to a preparation process of a flame retardant composition made from brominated bismuth and/or antimony compounds complexed with melamine, in which melamine, at least one between the bismuth carbonate and antimony sesquioxide, hydrobromic acid in aqueous solution are placed in contact with each other so as to trigger chemical reactions which lead to the formation of a complex of brominated bismuth or brominated antimony with melamine and melamine bromohydrate. The reagents are placed in contact in the presence of at least one reaction carrier defined by at least one compound chosen from the group consisting of melamine, melamine phosphate, melamine polyphosphate, ammonium phosphate, ammonium polyphosphate, triphenyl-phosphate, graphite, silica, lignin, coke and compounds containing triazine rings condensed or linked by —NH groups. The reaction carrier is not involved in the reactions. There are no polymeric compounds in quantities such as to create a polymer matrix. The reagents being introduced into the reactor in an amount defined by the stoichiometric ratios of said reactions. The reaction carrier is introduced into the reactor in an amount defined with respect to the total weight of the reagents so that it can perform a modulator function.

13 Claims, No Drawings

US 9,879,184 B2

PREPARATION PROCESS OF A FLAME RETARDANT COMPOSITION MADE FROM BROMINATED BISMUTH AND/OR ANTIMONY COMPOUNDS COMPLEXED WITH MELAMINE AND COMPOSITION OBTAINED THEREBY

This is a national stage application filed under 35 U.S.C. § 371 of international application PCT/IB2015/055691, filed under the authority of the Patent Cooperation Treaty on Jul. 28, 2015, published; which claims the benefit of European Patent Application No. 14425136.0, filed on Oct. 27, 2014. The entire disclosures of all the aforementioned applications are expressly incorporated herein by reference for all purposes.

FIELD OF APPLICATION

The present invention relates to a preparation process of a flame retardant composition made from brominated bismuth and/or antimony compounds complexed with melamine and a composition obtained by such process.

STATE OF THE ART

Bismuth/antimony bromide complexes with amines of various kinds, used as flame retardants, are known in the state of the art.

Such complexes suffer from the technical problems which typically afflict brominated organic compounds. In addition to the well-known environmental aspects the corrosiveness resulting from the tendency to release bromine or hydrogen bromide should be mentioned. The use of such compounds thus requires careful control of the intrinsic acidity of such additives (which may for example cause corrosion of equipment: extruder screws, dies, presses, etc. . . . ). Moreover, the tendency to decomposition of such brominated compounds reduces the self-extinguishing properties of the material incorporating them. This requires an increase in the effective amount of fire retardant in the dosing phase.

The U.S. Pat. No. 4,798,857 describes brominated or chlorinated compounds of bismuth or antimony complexed with amines of various kinds, having a good flame retardant action on thermoplastic polymers. Such complexes have the general formula R (MEX$_3$)$_y$ where R is an amine selected from the group consisting of dicyanamide, guanamine, 2-guanidinobenzimidazole, melamine, isophorone diamine, piperazine, optionally substituted with an alkyl, aryl or acyl group, and compounds containing from 2 to 9 triazine rings condensed or linked to each other by at least one —NH— group; Me is bismuth or antimony; X is chlorine or bromide; and y is a number between 0.3 and 4. These are pure, stoichiometrically defined complexes. Given the strictness of the stoichiometric formula the possibility of varying the content and the "type" of bromine or chlorine present, where required, is not contemplated. The preparation process of the complexes described in U.S. Pat. No. 4,798,857 in particular provides for the reaction of amines with metal halides, in particular BiBr$_3$, already prepared separately. This process is applicable on a laboratory scale, but not at an industrial level. Metal halides are, in fact, very unstable compounds, dangerous to handle, and as such subject to strict security restrictions. The handling of such compounds at an industrial level would require complex processing steps, not economically sustainable.

The U.S. Pat. No. 4,935,459 teaches in particular to produce flame retardant compositions made from halogenated compounds of bismuth and/or antimony complexed with melamine. Similarly to the provisions of U.S. Pat. No. 4,798,857 and therefore with the same operating limits, such complexes are produced using metal halides (in particular BiBr$_3$), prepared separately, as reagents.

A production process which uses separately prepared metal halides as reagents is also described in the scientific publication Costa et al. "*Thermal Degradation and Fire Retardancy of Antimony and Bismuth Trihalides-Melamine Complexes*", Polymer Degradation and Stability, 34 (1991) 55-73 and in the scientific publication Bertelli et al. "*Fire Retardant Systems Based on Melamine Hydrobromide: part I—Fire Retardant Behaviour*", Polymer Degradation and Stability, 18 (1987) 225-236.

The effectiveness of organic complexes of halogenated compounds of bismuth/antimony with amines as flame retardants has therefore been well-known for some time. The processes of synthesis are however applicable only in the laboratory on a small scale, and rarely industrially feasible given the volatile and dangerous nature of the reagents and of the products obtained.

The difficulties related to a large-scale production have in fact up to now made widespread use of such compounds impractical.

One industrial application of such compounds is described in the U.S. Pat. No. 5,166,235. The paper describes a masterbatch polypropylene matrix containing halogenated compounds of bismuth/antimony complexed with amines. The complexes are obtained in situ by reacting melamine and non-halogenated compounds of bismuth and/or antimony (in particular (BiO)$_2$CO$_3$ or SB$_2$O$_3$) with hydrohalogen acids (in particular HBr) in the polypropylene matrix. The process in particular makes it possible to prevent the separate production of metal halides. The process described in U.S. Pat. No. 5,166,235 has however the significant limitation of requiring control of the strength of the reactions, for example by working at reduced pressure. Such control is essential to prevent the degradation of the active substances and of the polymeric matrix.

The masterbatch described in U.S. Pat. No. 5,166,235 may only be used on polypropylene. This represents a significant limitation to the applicability of the above complexes. The masterbatch is moreover presented in the form of spherical-porous particles with relatively low load limits of the active principle (10-30%). There is therefore a "dilution effect" of the active principle by the polymer matrix which, while on the one hand partially obviating some of the aforementioned technical problems, on the other requires much higher quantities of additives during use to achieve flame retardancy. By operating this way, the disadvantage for the end user is that of having to take into account an unwanted polymer matrix which will influence the physical and rheological properties of the product. The polymer masterbatch is moreover partially irregular inasmuch as synthesised in the cavities of the porous polypropylene. Such cavities act as several independent reactors, originating differentiations in composition and the presence of small agglomerates difficult to disperse subsequently.

PRESENTATION OF THE INVENTION

Consequently, the purpose of the present invention is to eliminate entirely or in part the drawbacks of the prior art mentioned above, by making available a preparation process of a flame retardant composition made from brominated bismuth and/or antimony compounds complexed with melamine which is industrially applicable in a simpler way than the currently known processes.

A further purpose of the present invention is to provide a preparation process of a flame retardant composition made from brominated bismuth and/or antimony compounds complexed with melamine, which is easily controllable to avoid degradation of the active compounds.

A further purpose of the present invention is to provide a preparation process of a flame retardant composition made from brominated bismuth and/or antimony compounds complexed with melamine, which makes it possible to easily control the aggressiveness of the reagents, of the intermediates and of the reaction products.

A further purpose of the present invention is to provide a preparation process of a flame retardant composition made from brominated bismuth and/or antimony compounds complexed with melamine which makes it possible to obtain such composition in a pure form, free of polymer matrices, and thus utilisable as a general purpose active principle.

A further purpose of the present invention is to provide a preparation process of a flame retardant composition made from brominated bismuth and/or antimony compounds complexed with melamine, which makes it possible to obtain such composition with properties of chemical stability and limited aggressiveness.

A further purpose of the present invention is to provide a flame retardant composition made from brominated bismuth and/or antimony compounds complexed with melamine in a pure form, free of polymer matrices, and thus utilisable as a general purpose active principle.

A further purpose of the present invention is to provide a flame retardant composition made from brominated bismuth and/or antimony compounds complexed with melamine, which has properties of chemical stability and limited aggressiveness.

The technical characteristics of the invention according to the aforesaid purposes can be seen clearly from the contents of the following claims and the advantages thereof will be more clearly comprehensible from the detailed description below,

DETAILED DESCRIPTION

The present invention relates to a preparation process of a flame retardant composition made from brominated bismuth and/or antimony compounds complexed with melamine and the composition obtained by such process.

As will be clear from the following description, the flame retardant composition obtained using the process according to the invention is made from a mixture of a brominated compound of bismuth and/or antimony complexed with melamine and melamine bromohydrate.

According to a general embodiment, the preparation process according to the invention follows at least one of the two following reaction schemes:

$$Bi_2CO_5 + 6HBr \rightarrow 2BiBr_3 + 3H_2O + CO_2$$

$$BiBr_3 + ML \rightarrow complex\ ML/BiBr_3$$

$$HBr + ML \rightarrow MHB \quad \text{(I)}$$

or $$Sb_2O_3 + 6HBr \rightarrow 2SbBr_3 + 3H_2O$$

$$SbBr_3 + ML \rightarrow complex\ ML/SbBr_3$$

$$HBr + ML \rightarrow MHB \quad \text{(II)}$$

where ML indicates melamine and MHB indicates melamine bromohydrate.

The two reaction schemes essentially differ only in the type of salt used as an initial reagent for the supply of the metal, i.e. bismuth carbonate ($Bi_2CO_5$) or antimony sesquioxide ($Sb_2O_3$). The other reagents are the same, i.e. melamine and hydrobromic acid.

Preferably the preparation process follows only one of the above two reaction schemes, introducing into the reaction only one between the bismuth carbonate ($Bi_2CO_5$) or the antimony sesquioxide ($Sb_2O_3$). However, it is possible to implement the process by introducing into the reaction both bismuth carbonate ($Bi_2CO_5$) and antimony sesquioxide ($Sb_2O_3$), thus following both the reaction schemes.

Both reaction schemes comprise two main reactions.

A first reaction relates to the synthesis of the ML/BiBr$_3$ complex and divides in turn into two reactions that lead in sequence to the formation of an intermediate consisting of the metal bromide through the attack of the metal salt by the acid (as well as the formation of by-products—only water or water and $CO_2$—which are then removed from the reaction environment), and then the combination of said intermediate with melamine to form the complex.

The second reaction, which takes place simultaneously with the first, relates to the synthesis of melamine bromohydrate, through the attack of the melamine by the acid.

The formation of the intermediate BiBr$_3$ is vigorous and exothermic and develops a strongly acid environment. In addition, the careless handling of Br$_2$ and HBr in the presence of bismuth or antimony or their inorganic salts may even generate uncontrolled reactions of combustion or explosion. In addition, the intermediates and reaction products involved, in particular the bromides of the metals and the complexes of such brominated compounds are characterised by high aggressiveness and instability.

The formation process according to the invention has made it possible to solve simply and effectively both the problem of controlling the exothermy and the problem of managing the characteristics of the intermediates and final products, making production at industrial level of such products possible and safe.

In particular, contrary to what is provided for by U.S. Pat. No. 5,166,235, the process can be conducted at atmospheric pressure and not at reduced pressure, with benefits in terms of simplification of the plant and control.

Such preparation process comprises the following general operating steps:

a) providing the reagents provided for according to one of said two reaction schemes: melamine; at least one between bismuth carbonate and antimony sesquioxide; and hydrobromic acid in an aqueous solution;

b) placing the above reagents in contact with each other in a reactor so as to trigger said chemical reactions and obtain a complex of brominated bismuth or brominated antimony with melamine and melamine bromohydrate.

As reactor, in particular, a blade mixer with heating/cooling jacket may be used.

In particular, the aqueous solution of hydrobromic acid has a concentration in weight of hydrobromic acid between 40% and 60%.

According to the invention the process comprises a step c) of providing at least one reaction carrier defined by at least one compound selected from the group consisting of melamine, melamine phosphate, melamine polyphosphate, ammonium phosphate, ammonium polyphosphate, graphite, silica, lignin, triphenylphosphate, coke and compounds containing triazine rings condensed or linked by —NH groups.

Preferably, as compounds containing triazine rings condensed or linked by —NH groups known compounds such as melam (2,2'-iminobis [4,6-diamine-1,3,5-triazine]; $C_6H_9N_{11}$ CAS: 3576-88-3), melem (1,3,4,6,7,9,9'-heptaazaphenalene-2,5,8-triamine; $C_6H_6N_{10}$ CAS: 1502-47-2) and melon (CAS: 32518-77-7) are used.

According to an essential aspect of the invention the reagents provided in step a) are placed in contact in step b) in the presence of at least one compound provided in step c) which acts as a reaction carrier.

The reaction carrier is not involved in said reactions, and remains almost chemically and physically unchanged.

As will be clarified in the rest of the description, the presence of such a reaction carrier is essential because it allows the reactions to proceed smoothly and uniformly towards their completion, resolving the problems noted in the prior art.

The identification of said one or more reaction carriers has made it possible to industrialise the preparation process of brominated compounds of bismuth and/or antimony complexed with melamine, supporting reactions which would otherwise be unmanageable on a large scale.

The use of the reaction carriers defined by the present invention has also made it possible to obtain such complexes in the form of formulations that make them easily utilisable, since they do not have residual corrosivity, are chemically stable and do not present problems of photosensitivity.

The flame retardant compositions obtained with the process according to the invention show enhanced flame retardancy properties compared to similar compositions made from the aforesaid complexes. This is attributable to the combined presence of the $ML/MeBR_3$ complex and the melamine bromohydrate in the final composition.

Advantageously, the step b) in which the reagents are placed in contact with each other may take place in the presence of only one reaction carrier, preferably melamine, or of two or more different reaction carriers.

In the case in which melamine is used as a reaction carrier, alone or in combination with other compounds, the total quantity of melamine introduced into the reactor is in excess of the stoichiometric amount required in relation to the quantities of the other reagents. In other words, the melamine will be introduced in such quantity as to itself (alone or together with the further reaction carrier) constitute a support as well as the main reagent for the formation of the flame retardant complex. At the end of the reactions, part of the melamine introduced will in turn be brominated, while the amount stoichiometrically in excess will remain almost unchanged chemically and physically.

The reaction carrier may thus be: melamine alone, in excess of the stoichiometry indicated in the aforementioned reactions; or mixtures of melamine with melamine phosphate, melamine polyphosphate, ammonium polyphosphate, graphite, silica, lignin, triphenyl phosphate, coke and compounds containing triazine rings condensed or linked by —NH groups (melam, melem, melon for example); or one or more of the compounds selected from melamine phosphate, melamine polyphosphate, ammonium polyphosphate, graphite, silica, lignin, triphenyl phosphate, coke and compounds containing triazine rings condensed or linked by —NH groups (melam, melem, melon for example), without melamine in excess.

According to the invention, said reagents (melamine; at least one between bismuth carbonate and antimony sesquioxide; and hydrobromic acid in aqueous solution) are introduced into the reactor in an amount defined by the stoichiometric ratios according to one of the aforesaid two reaction schemes.

As already mentioned above, the formation of the complex ($ML/BiBr_3$ and/or $ML/SbBr_3$) is independent of the formation of melamine bromohydrate. This makes it possible to modulate the final content of complex and of melamine bromohydrate in the final composition, varying the initial amount of the metal salt and of the melamine. The stoichiometric ratios therefore relate to the amount of the metal salt in relation to the hydrobromic acid and to the melamine for the formation of the complex, and to the amount of melamine in relation to the hydrobromic acid for the formation of the melamine bromohydrate.

The bromination of part of the melamine makes it possible to have the simultaneous presence of "two types" of bromine with different stoichiometries and effects in terms of flame retardant action. Depending on the type of polymer or, more generally, the type of application the flame retardant composition according to the invention is intended for, it is possible to vary the ratio between the two types of bromine.

According to the invention, the reaction carrier is introduced into the reactor in an amount defined with respect to the total weight of the reagents so that it can perform a modulator function.

Since the reaction carrier acts as a "modulator" of the vigour of the reactions, but is not involved in any of these, it is not tied to these by any stoichiometry. The reaction carrier need only be present in weight in minimum quantities such as to be able to perform its "modulator" function.

"Reaction modulator" is understood to mean one or more compounds which in terms of physical and chemical characteristics (i.e. stability in reaction conditions, chemical compatibility, etc. . . . ) and/or due to their ponderal presence remain inert during the synthesis of the brominated components creating however the conditions (temperature, pH, level of chemical inertia, etc. . . . ) such as to make such reactions, per se excessively vigorous, realisable simply and safely at the industrial level.

The amount in weight of the reaction carrier may vary depending on the type of compound or compounds selected.

Preferably, the reaction carrier (whether defined by a single compound or two or more compounds) is introduced in an amount of not less than 8% in weight with respect to the total weight of the reagents. As described further below, in the final product—following the removal of some reaction by-products such as water or $CO_2$—said minimum weight of the reaction carrier is raised to 10% in weight.

According to the invention, polymeric compounds are not introduced in the reactor, at least not in such quantities as to create a polymer matrix. Small amounts of polymers may possibly be present, but not in such quantities as to form a polymer matrix such as to limit the use of the flame retardant composition to specific polymers. In particular, any polymers may be present in amounts not exceeding 3% in weight of the total weight of the flame retardant composition. In particular, polymeric resins may be present as compatibilizing agents, protective agents and more generally as "improvement additives" of the applicability of the flame retardant composition of the invention.

This way, as will be clarified in the rest of the description, the flame retardant composition according to the invention is utilisable as a general purpose active principle.

Preferably, the reagents are placed in contact with each other in the presence of the reaction carrier under continuous stirring.

The reagents and reaction carrier can be introduced into the reactor simultaneously. However, a mode with temporally differentiated introduction of the reagents is preferred to this—theoretically possible—operating mode.

Preferably, the contact between the reagents in the presence of the reaction carrier takes place in two distinct sub-steps:
b1) introducing into the reactor the melamine, the reaction carrier and at least one between the bismuth carbonate and antimony sesquioxide under continuous stirring to form a mixture; and
b2) adding to the aforesaid mixture under continuous stirring the hydrobromic acid in aqueous solution so as to trigger the aforementioned chemical reactions.

Regardless of the mode and sequence of introduction of the reagents in the reactor, the preparation process of the flame retardant composition made from brominated compounds of bismuth and/or antimony complexed with melamine is a "one step" process in the sense that the separate preparation of the brominated compounds of bismuth or antimony is not provided for, but all the reactions take place in the same reaction environment. This makes the process industrially easier to manage.

The process according to the invention can also be defined as a process that takes place in situ, in the sense that none of the reaction products, in particular the more unstable or potentially dangerous, is prepared or handled out of the reactor.

Advantageously, as will be described in more detail below, the preparation process according to the invention may be conducted through a dry or semi-dry pathway or through a wet pathway. The choice between the two pathways is carried out mainly by acting on the introduction mode of the bromide acid in the reactor, as well as on the initial physical state of the reagents.

The dry or semi-dry pathway is chosen in the case of wishing to maintain throughout the reaction a physical form of the raw reaction product that can be processed in a mixer for powders (thus in the form of a paste or semi-dry at each step). In this case, the modulation of the rate of addition of the acid is a key point in the management of the economy of the process.

The wet pathway process is chosen, instead, in the case in which there is a need or interest in having a liquid raw reaction product, so as to achieve a greater product homogeneity. As will be clarified below, the wet pathway process combined with a spray-drying technique makes it possible to obtain dry products in the form of powders with particular particle sizes without the need for further processing of the final product, such as micronisation. In this case, the modulation of the rate of addition of the acid is not a key point in the management of the economy of the process. Compared to the dry pathway it is possible to dose the acid faster or, possibly even introduce it into the reaction environment all together.

According to a first particular embodiment of the process according to the invention, relative to the dry or semi-dry pathway, the melamine, the reaction carrier and at least one between the bismuth carbonate and antimony sesquioxide are introduced into the reactor in the dry state, preferably in the form of powders.

Preferably, inside the reactor the melamine, the reaction carrier and at least one between the bismuth carbonate and antimony sesquioxide are subjected to continuous stirring.

Advantageously, before the addition of the hydrobromic acid, the mixture of melamine, the reaction carrier and at least one between the bismuth carbonate and antimony sesquioxide is preheated. Preferably, the powders are preheated to a temperature between 60° C. and 90° C. It has been found experimentally that this range of temperatures, even considering the residual exothermy of the reaction, permits an optimal evaporation of the water once the hydrobromic acid has reacted. This temperature range also represents a good compromise between production costs (to heat the reactor) and the requirements of said process.

Thanks to the preheating of the powders, the evaporation of water right from the earliest stages of dosing the aqueous solution of hydrobromic acid is favoured, and the reaction mass is thus maintained in a semi-dry or mixable paste state.

Preferably, the hydrobromic acid in aqueous solution is added to the mixture of melamine, reaction carrier and at least one between the bismuth carbonate and antimony sesquioxide following a controlled dosage, in order to keep the mass of reagents and reaction products always in a semi-dry form or in the form of a workable paste. The controlled dosage of the aqueous solution of hydrobromic acid prevents an abrupt increase in the water content in the mass of reagents. Thanks to the phenomenon of evaporation of the water induced by the exothermy of the reactions, it is thus possible to limit the water content in the mass of reagents and reaction products.

Preferably, the controlled dosage of the acid is anticipated by a preheating of the powders. As already anticipated, the preheating of the powder helps to promote the evaporation of water gradually as the aqueous solution of acid is added and water is formed as a reaction product.

In particular, the hydrobromic acid in aqueous solution (preferably 40%-60% in weight of hydrobromic acid) is dosed in the dry state mixture with a ponderal dosing rate of between 8 and 11%/h of the total weight of the reagents and reaction carrier.

Advantageously, the mass of reagents and reaction carrier is kept under continuous stirring during and after the dosing of the acid.

The pathway of formation of the reaction products and their maintenance in a more or less fine solid form is thus guided by the regularity and rate of addition of the aqueous solution of the hydracid, and by the heating of the mass kept in movement by the action of the kneading blades. This way, the water of the hydracid and that of the reaction will be removed from the mixture gradually as it is added and/or formed, thus ensuring stoichiometry and uniformity of result.

Advantageously, after having added the whole amount of hydrobromic acid, the reactor is heated to remove all the water present and fully dry the reaction products, thus obtaining a dry raw product. In particular, the reactor is heated to a temperature between 100° C. and 140° C. Such temperatures are sufficient to ensure the desired drying in "industrially reasonable" times (e.g. in the case of a batch of 1000 kg the raw product is dried in about 2 hours). The temperature may be increased up to about 240° C. to reduce the drying times, without damaging the reaction product. Heating to 240° C. is not preferred, however, given the high costs needed to bring a large mass to a higher temperature.

This way at the end of the reaction a 100% pure powder is obtained which has not to undergo industrially complex treatment such as, for example, filtration, recovery of the active principle from the liquid, distillation, etc. . . . .

Advantageously, the dry raw product obtained at the end of heating is subjected to a micronisation process, aimed at obtaining powders with the desired particle size.

Preferably this micronisation process is conducted to bring the particles of the solid raw product to have a uniform mean particle size. Preferably the mean particle size is between 5 µm-50 µm, more preferably between 20 µm-30 µm or between 5 µm-10 µm.

Advantageously, following the dry or semi-dry pathway specific additives can be introduced before, during or after the dosing of the hydrobromic acid in the reactor.

In particular, compatibilising/water-repellent agents and/or agents facilitating the handling of the finished product in the application phase thereof to the intended matrix may be introduced, preferably at the end of the reactions, i.e. at the end of the dosing of the acid.

In particular, after the complete drying of the reaction products and prior to the micronisation process, at least one water repellent agent or compatibilizer, consisting in particular of one or more compounds having a softening point between 60° C. and 100° C., such as paraffin or polyester waxes preferably stearic acid, may be added to the dry raw product.

Advantageously, after the complete drying of the reaction products and before the micronisation process, at least one agent capable of favouring the handling of the finished product in the application phase of the latter to the intended matrix, such as silica, may be introduced into the reactor.

According to a second particular embodiment of the process according to the invention, relative to the wet pathway, the melamine, the reaction carrier and at least one between the bismuth carbonate and antimony sesquioxide are introduced into the reactor preferably in the form of powders, together with the water, obtaining a suspension. Preferably, inside the reactor the melamine, the reaction carrier, at least one between the bismuth carbonate and antimony sesquioxide and the water are subjected to continuous stirring.

Advantageously, unlike the dry or semi-dry pathway, it is not necessary to preheat the melamine, metal salt and reaction carrier in the aqueous suspension.

The water is present in an amount such as to ensure that after the addition of the hydrobromic acid, the reactions take place in solution.

Preferably, the hydrobromic acid in aqueous solution is added to the aforesaid suspension in water of melamine, of the reaction carrier, and of at least one between the bismuth carbonate and antimony sesquioxide without heating the reactor.

In the case of the wet pathway, the modulation of the rate of addition of the acid is not a key point in the management of the economy of the process. Compared to the dry pathway it is possible to dose the acid faster or, possibly even introduce it into the reaction environment all together.

Preferably, the hydrobromic acid in aqueous solution is added to the aforesaid suspension adopting a controlled dosage which is functional to optimal management of the process, in particular in terms of handling the reagent (for example by means of pumps), of observance of safety procedures and of control of the chemical reactions.

Advantageously, the mass of reagents and reaction carrier is maintained in continuous stirring during and after the dosing of the acid.

After adding the whole amount of hydrobromic acid, a raw reaction product in aqueous suspension is obtained.

Preferably, after adding the whole amount of hydrobromic acid, the raw reaction product in aqueous suspension is subjected to drying to obtain a dry raw product.

The drying of the aqueous suspension may be carried out using any technique suitable for the purpose, such as vacuum drying or drying in rotating cylinders, by means of suitably chosen ovens, evaporators, etc. The drying step is then followed by a micronisation step aimed at bringing the particles of the dried raw product to have a uniform mean particle size. Preferably, the mean particle size is between 5 µm-50 µm, more preferably between 20 µm-30 µm or between 5 µm-10 µm.

Preferably, the drying is achieved by pulverisation drying or a spray drying technique, which makes it possible to dry the aqueous suspension to obtain a dry product with a uniform particle size without a micronisation step. The spray-drying technique, in fact, permits very flexible control of the properties of the particles of powder such as particle size, density, moisture content, etc. . . . ; for this reason, if properly applied, it makes it possible to avoid steps which could prove industrially costly such as the crushing and micronisation of the finished product.

Substantially, the "spray drying" technique (in itself known to a person skilled in the art) is based on the possibility of producing powders of a controlled particle size and shape directly from an aqueous suspension by evaporation of the solvent. The process is based on mixing a heated gas (usually steam) with an atomized liquid, thus physically composed of droplets with a high surface/mass ratio (thus maximising the heat exchange) inside a container (drying chamber) and determining, by direct contact, the rapid and uniform evaporation of the solvent present in the liquid.

The process of pulverisation or spray drying comprises three stages: atomization of the liquid to be dried; drying; and separation of the powder obtained from the wet gas. This type of technique determines a considerable thermal shock to the products to be dried. The flame retardant composition of the present invention, as will be described below, however, has shown thermal and chemical characteristics such as to advantageously allow the use of such drying technique in the last step of the wet pathway process.

Advantageously, thanks to the excellent thermal properties of the flame retardant composition according to the invention, the aqueous suspension can be dried using a spray drying technique known as "gatedrier". The "gatedrier" (in itself known to a person skilled in the art) is a spray dryer improved in size and performance. The peculiarity of the gatedrier is its ability to work with input temperatures of the hot air even 50° C. higher than in normal spray drying techniques (for reasons of savings in time and energy).

Advantageously, the water content of the aqueous suspension can be regulated depending on the conditions of viscosity required by the drying treatment, in particular in the case of pulverization or spray drying.

Advantageously, after the drying process, the raw dry product may be treated with at least one water repellent agent and/or compatibilizer, preferably having a softening point between 60° C. and 100° C. such as paraffin waxes, preferably stearic acid. Advantageously, after the drying process, the raw dry product may be treated with at least one agent, such as silica, capable of favouring the handling of the finished product in the application phase thereof to the matrix for which it is intended.

Some examples of preparation of a flame retardant composition according to the process of the present invention are given below.

The bromine content of the flame retardant composition was determined by acid-base titration, dispersing 0.5 g of the composition in 100 ml of water, under magnetic stirring, heating to 50° C. and then adding a few drops of phenolphthalein. The suspension thus obtained was titrated with a 0.1 N solution of NaOH.

Example 1 (Dry or Semi-Dry Synthesis)

500 kg of melamine $C_3H_6N_6$ and 100 kg of bismuth basic carbonate $(BiO)_2CO_3$ were introduced under agitation into a "four wire coils" mixer with jacket, with a capacity of about 1500 liters, fitted with a heating and cooling system. Heating of the oil in the jacket is performed until the powders reach a temperature of 75-80° C. Once reached this temperature, 434 kg of aqueous solution of hydrobromic acid 48% HBr were dosed by means of a membrane pump at the rate of about 90 kg/h (which corresponds to about 10% w/w/h). During the dosing of the acid (i.e. in conjunction with the development of the reactions), the raw reaction product remains at all times in the semi-dry state and the temperature rises to settle around 100-105° C. (optimum temperature for the evaporation of the secondary product: water).

After dosing the acid the reactor is heated up to bring the "vapours" to about 120° C. and thus achieve the removal of all the water still present in the reaction environment and the complete drying of the raw product. The pH of the water coming from the condenser of the reactor is measured. This pH remains substantially neutral throughout the entire reaction, proving that all the fed hydrobromic acid enters into the reaction and that the by-products leaving the reactor do not retain significant residual acidity.

Still at the temperature of 120° C., 8 kg (about 1% in weight of the total) of stearic acid is then added to give water-repellence to the finished product, the heating is interrupted and the product is left to cool spontaneously under agitation inside the reactor. At this point, to make the powder in question more "fluid" 1.6 kg of silica (about 0.2% in weight of the total) is added and left to mix for a further 30 min. The product is then micronised with $d_{95}$<30 microns. The product thus obtained has a bromine content of about 26%, a pH in aqueous suspension of about 5.7 and a thermal resistance above 230° C. (loss ≤2% after 15 min of permanence in a muffle furnace with air circulation at this temperature).

850 kg of finished product are obtained having the following composition in weight: 36.5% melamine bromohydrate; 28.5% melamine/$BiBr_3$ complex; 35% melamine; total bromine=26%.

Example 2 (Wet Synthesis)

In a pilot mixer (paste and liquid-tight) with a capacity of about 150 liters and fitted with a heating/cooling jacket, the following are introduced with vigorous stirring: 25 kg of melamine, 5 kg of bismuth basic carbonate and 61 kg of water. To this suspension, kept in agitation and making cooling oil circulate in the jacket, 21.7 kg of aqueous solution of 48% HBr are added. During the dosing of the acid the temperature never exceeds 70° C. The resulting suspension (pH=5.5) is then sprayed in a "gate" drier at a pressure of 16 MPa and an output temperature of 95° C.

40 kg of finished product are obtained in powder form, which may possibly be treated with stearic acid for water-repellence and to increase compatibility with the polyolefins and treated with silica to increase its fluidity in handling, with the following composition in weight: 36.5% melamine bromohydrate; 28.5% melamine/$BiBr_3$ complex; 35% melamine; total bromine=26%.

Example 3

In a pilot mixer with a capacity of about 150 liters, 50 kg of melamine and 10 kg of bismuth sub-carbonate kept under vigorous agitation are heated to 75-80° C. As in Example 1, the acid aqueous solution is dosed at a rate of 10% w/w/h, this time in the amount of 67.7 kg, so as to keep the raw reaction product always in the semi-dry state. The pH of the "recondensed" water is checked and kept neutral in all the steps. The temperature inside the reactor is kept below 105° C. throughout the dosing of the acid.

90 kg of product are obtained with the following composition in weight: 64.3% melamine bromohydrate; 24.7% melamine/$BiBr_3$ complex; 11% melamine; total bromine=35%; pH in aqueous suspension=5.2.

Compared to Example 1, the ratios of the reagents have been modified to increase the bromine content of the MHB component.

Example 4

With the same procedures and equipment as Example 3, 40 kg of melamine are reacted with 25 kg of bismuth carbonate and 65 kg of aqueous solution of 48% HBr. The raw reaction product remains in the semi-dry state at all times and the water in output from the condenser has a neutral pH during all steps of the process. The maximum temperature reached during the reaction remains below 105° C.

90 kg of finished product are obtained having the composition: 20.5% melamine bromohydrate; 61.8% melamine/$BiBr_3$ complex; 17.7% melamine; total bromine=34%; pH in aqueous suspension=5.

Compared to Example 1, the ratios of the reagents have been modified to increase the bromine content of the ML/BiBr3 complex component.

Example 5 (Use of Sb)

With the same procedures and equipment as Example 3, 50 kg of melamine are reacted with 6.25 kg of antimony sesquioxide and 43.2 kg of 48% aqueous solution of HBr. The raw reaction product remains in the semi-dry state at all times and the water in output from the condenser has a neutral pH during all steps of the process. The maximum temperature reached during the reaction remains below 105° C.

113 kg of product are obtained with the following composition in weight: 35.2% melamine bromohydrate; 29.8% melamine/BiBr3 complex; 35% melamine; total bromine=27%; pH in aqueous suspension=5.4.

Example 6 (Use of Reaction Carriers Other than Melamine)

With the same ways and equipment as example 3, 5 tests are conducted using as a "reaction carrier" the compounds and amounts as specified below:

a) 23 kg of melamine, 27 kg of Melamine phosphate, 10 kg of bismuth subcarbonate and 43.4 kg of an aqueous solution of 48% HBr. 80 kg of finished product are obtained with a composition in weight: 36.3% melamine bromohydrate; 28.4% melamine/$BiBr_3$ complex; 35.3% melamine phosphate; total bromine 26.1%.

b) 23 kg of melamine, 27 kg of Melamine polyphosphate, 10 kg of bismuth subcarbonate and 43.4 kg of an aqueous solution of 48% HBr. 80 kg of finished product are obtained having the composition: 36.3% melamine bromohydrate; 28.4% melamine/$BiBr_3$ complex; 35.3% melamine polyphosphate; total bromine=26%.

c) 23 kg of melamine, 27 kg of ammonium polyphosphate, 10 kg of bismuth subcarbonate and 43.4 kg of an aqueous solution of 48% HBr. 80 kg of finished product are obtained with a composition in weight: 36.3% melamine bromohydrate; 28.4% melamine/$BiBr_3$ complex; 35.3% ammonium polyphosphate; total bromine=26.2%.

d) 23 kg of melamine, 27 kg of graphite, 10 kg of bismuth subcarbonate and 43.4 kg of an aqueous solution of 48% HBr. 80 kg of finished product are obtained with a composition in weight: 36.3% melamine bromohydrate; 28.4% melamine/$BiBr_3$ complex; 35.3% graphite; total bromine=26.2%.

e) 36.5 kg of melamine, 13.5 kg of silica, 10 kg of bismuth sub-carbonate and 43.4 kg of an aqueous solution of 48% HBr. 80 kg of finished product are obtained having the composition: 36.3% melamine bromohydrate; 28.4% melamine/$BiBr_3$ complex; 17.5% silica; 17.8% melamine; total bromine=25.8%.

The reaction temperature observed during the performance of the batches indicated in example 6 is kept in each case below 105° C. and the pH of the individual finished products reported is confirmed in each case as between 5 and 6.

All examples 1 to 6 reported above were conducted at atmospheric pressure.

The monitoring of the pH of the water in output from the reactor and of the suspension containing the finished product confirms the fact that the products and by-products of the reaction obtained using the process according to the invention have residual mild acidity (pH not lower than 5). From the experimental data it can be seen that at the end of the reactions in the reactor there is a very low level of acidity, due to the fact that the acid has completely reacted. Lastly, it may be concluded that in working conditions, the reaction product presents substantially no acidity. This evidence can be expressed in other terms such as "limited aggressiveness" which will presumably have a very positive impact on the "average life" of the plants of production and subsequently on the plants of processing/application of the brominated complexes thus obtained.

The present invention also relates to a flame retardant composition made from brominated bismuth and/or antimony compounds complexed with melamine.

Preferably, but not necessarily such a composition is obtained using the process according to the present invention.

According to the invention, the flame retardant composition, is composed of:
  a complex having a formula ML (MeBr3), where ML indicates melamine and Me is bismuth or antimony;
  melamine bromohydrate;
  at least one among the compounds chosen from the group consisting of melamine, melamine phosphate, melamine polyphosphate, ammonium phosphate, ammonium polyphosphate, graphite, silica, lignin, triphenylphosphate, coke and compounds containing triazine rings condensed or linked by —NH groups; and possible additives.

Preferably, as compounds containing triazine rings condensed or linked by —NH groups known compounds such as melam (2,2'-iminobis [4,6-diamine-1,3,5-triazine]; $C_6H_9N_{11}$ CAS: 3576-88-3), melem (1,3,4,6,7,9,9'-heptaazaphenalene-2,5,8-triamine; $C_6H_6N_{10}$ CAS: 1502-47-2) and melon (CAS: 32518-77-7) are used.

Preferably, the composition is in the form of dry powder, with mean particle size between 5 µm-50 µm. Preferably the particle size is between 20 µm-30 µm or between 5 µm-10 µm.

Advantageously the flame retardant composition does not comprise polymeric compounds, at least not in such quantities as to create a polymer matrix. Small amounts of polymers may possibly be present, but not in such quantities as to form a polymer matrix such as to limit the use of the flame retardant composition to specific polymers. In particular, any polymers may be present in amounts not exceeding 3% in weight of the total weight of the flame retardant composition. In particular, polymeric resins may be present as compatibilizing, protective agents and more generally as "improvement additives" of the application of the flame retardant composition of the invention.

As will be explained in the rest of the description, with reference to experimental tests conducted, the flame retardant composition according to the invention gives excellent flame-retardant properties to the polymers it is dosed in. Such properties emerge even at low dosages.

The flame retardant composition according to the invention has no residual aggressiveness, is chemically stable and does not present the problems of photosensitivity emerging for example in the scientific publication Costa et al. "Thermal Degradation and Fire Retardancy of Antimony and Bismuth Trihalides-Melamine Complexes", Polymer Degradation and Stability, 34 (1991) 55-73. Moreover, the flame retardant composition according to the invention has a considerable versatility of use resulting from the possibility of varying the "type and content" of bromine present depending on the needs and specific affinities of the single component (complex or melamine bromohydrate) with the chosen matrix (polymer type, resin type, etc. . . . ).

According to a general embodiment of the invention, the flame retardant composition is composed of:
  20-65% in weight of the aforesaid complex ML (MeBr3);
  20-65% in weight of melamine bromohydrate;
  10-40% in weight of at least one among the compounds chosen from the group consisting of melamine, melamine phosphate, melamine polyphosphate, ammonium phosphate, ammonium polyphosphate, graphite, silica, lignin, triphenyl-phosphate, coke and compounds containing triazine rings condensed or linked by —NH groups;
  0-3% of additives.

According to a first particular embodiment, the flame retardant composition is composed of:
  25-35% in weight of the aforesaid complex ML (MeBr3);
  25-35% in weight of melamine bromohydrate;
  25-30% in weight of at least one among the compounds chosen from the group consisting of melamine, melamine phosphate, melamine polyphosphate, ammonium phosphate, ammonium polyphosphate, graphite, silica, lignin, triphenyl-phosphate, coke and compounds containing triazine rings condensed or linked by —NH groups;
  0-3% of additives.

This first embodiment is particularly suitable to be used in applications in which, in addition to the fire retardant (FR) action performed by the two types of bromine present roughly in the same quantities, the presence of a significant amount of reaction carrier (about one third) acquires a central role. "Central role" may, for example, be understood as a modulation of the residual chemical aggressiveness of the additive on the operators, in particular in the case in which the reaction carrier comprises melamine, silica, lignin, etc. . . . ; or an FR-synergic action supplied, for example, in the case in which the reaction carrier comprises phosphates; or even an effect on the total thermal conductivity in the case in which the reaction carrier comprises graphite or coke, and so forth.

According to a second particular embodiment, the flame retardant composition is composed of:
- 55-65% in weight of said complex having the formula ML (MeBr3);
- 20-25% in weight of melamine bromohydrate;
- 10-20% in weight of at least one among the compounds chosen from the group consisting of melamine, melamine phosphate, melamine polyphosphate, ammonium phosphate, ammonium polyphosphate, graphite, silica, lignin, triphenyl-phosphate, coke and compounds containing triazine rings condensed or linked by —NH groups;
- 0-3% of additives.

This second embodiment is particularly suitable to be used when the matrix (polymeric or otherwise) in which the flame retardant composition is incorporated, in addition to requiring a given intake of total bromine, is also particularly sensitive to the flame retardant action of the complex of formula ML (BiBr3) and chemically similar to it.

According to a third particular embodiment, the flame retardant composition is composed of:
- 20-25% in weight of said complex having the formula ML (MeBr3);
- 55-65% in weight of melamine bromohydrate;
- 10-20% in weight of at least one among the compounds chosen from the group consisting of melamine, melamine phosphate, melamine polyphosphate, ammonium phosphate, ammonium polyphosphate, graphite, silica, lignin, triphenyl-phosphate, coke and compounds containing triazine rings condensed or linked by —NH groups;
- 0-3% of additives.

This third embodiment is particularly suitable to be used when the matrix (polymeric or otherwise) in which it is incorporated, in addition to requiring a given intake of total bromine, is also particularly sensitive to the anti-flame action of the melamine bromohydrate and chemically similar to it.

Preferably, the flame retardant composition is composed of: the complex ML (MeBR$_3$); melamine bromohydrate; melamine; and possible additives. Preferably, the compositions in weight of the various components correspond to those indicated in the embodiments described above.

In particular, the additives may consist of compatibilizing/water-repellent agents and/or agents which facilitate the handling of the composition in question at the application stage thereof to the matrix for which it is intended, such as silica.

In particular, the water-repellent/compatibilizing agents are preferably one or more compounds having a softening point between 60° C. and 100° C., such as paraffin waxes or a polyester, preferably stearic acid.

As previously indicated, the flame retardant compositions according to the invention, in particular those obtained using the preparation process according to the invention, may exert a strong action as flame retardants in many polymeric materials, such as, polypropylene and its copolymers, polystyrene (crystal and buffer), nylon 6 and 66, PBT.

To evaluate the effectiveness of the flame retardant compositions according to the invention some tests were conducted on specimens of polymers to which such compositions were added.

The polymer mixtures with the flame retardant compositions according to the invention added to them were obtained by mixing in a Brabender mixer, at a temperature equal to or higher than the softening temperature of the polymer they were destined to.

The polymeric mixtures added contain from 1 to 30% in weight of the flame retardant composition according to the invention and from 0 to 1% in weight of a promoter of free radicals, such as 2,3-dimethyl-2,3-diphenyl butane or poly 1,4-diisopropyl benzene, or others of the same type/function.

In general, the radicals promoter is usually introduced into the compound to stimulate "dripping", which is one of the mechanisms by means of which a flame retardant can carry out its function. Flame retardants which act only by "dripping" do not exert their function except in the presence of a radicals promoter, other retardants instead work equally well in the absence of a radicals promoter (using other mechanisms). The flame retardant properties according to the invention were verified by investigating behaviour both in the presence and absence of radicals promoters. Where required and permitted, the radicals promoter also makes it possible to significantly lower the amount used of the flame retardant.

The compounds thus obtained are converted, by moulding, into plates with a thickness of 3.2 mm from which the specimens (123 mm×13 mm) are cut for measuring flame resistance.

The level of flame resistance was determined by measurements of the Index of oxygen (in compliance with ASTM 2863) and/or by determining the extinguishing time by application of the standard UL-94 (Underwriter Laboratories—USA)

The oxygen index (CI) represents the minimum concentration of oxygen (expressed in % volume) in an oxygen-nitrogen mixture which allows the sample of the test material, after ignition with a butane gas burner, to continue to burn for three minutes and/or for 50 mm of its length: the higher the value of the oxygen index (CI), the greater its flame-resistance.

The UL-94 test is conducted on samples placed vertically and having different thicknesses coded by the method. As already mentioned, the tests used only specimens of 3.2 mm thickness, corresponding to the eighth of an inch described in the standard. The burner flame is placed in contact with the lower edge of the sample at an angle of 45°. From the moment it is removed, the time in which the specimen stops burning and whether it lets drops of molten polymer fall during combustion, is recorded.

Based on its behaviour, the material is thus classified:
V-0: when the extinguishing time of the flame is less than or equal to 5 seconds (mean value of 5 samples for 2 consecutive ignitions). No flaming droplets should fall.
V-1: when the extinguishing time is less than or equal to 25 sec. No flaming droplets should fall.
V-2: when, although extinguishing itself, the sample lets flaming droplets fall able to ignite a ball of cotton wool placed 30 cm under it.

Sample Preparation and Characterization of Flame Retardancy (FR) Performance

In order to evaluate their performance as flame retardants, polymeric mixtures were prepared containing the flame retardant compositions as obtained from the examples 1-7 according to the process of the invention already described. The samples to be subjected to the flame resistance test are prepared in a Brabender laboratory mixer working at a speed of 30 rpm and with a chamber temperature of 180° C. and a temperature of the circulating oil kept at 220° C.

The quantity and nature of the various components is been indicated in the tables below together with the flame resistance results. In particular, Tables 1 and 2 report the results of the flame-resistance tests conducted on polymeric formulations containing different thermoplastic materials and flame retardant composition obtained from the application of the process according to the invention as in example 1. Tables 3 and 4 instead shows the flame resistance data of the polymeric formulations containing flame retardant compositions prepared according to examples 1-6 and the sole polypropylene Moplen HF501N.

The following materials were used:
Moplen® HF501N PP: polypropylene marketed by LyondellBasell;
Dutral CO054: ethylene-propylene copolymer (60% ethylene) marketed by Versalis Spa;
Edistir N1840: crystal polystyrene marketed by Versalis Spa;
Pibiflex 2560: polyester marketed by P-GROUP Spa;
CCPIB: poly-1.4-diisopropylbenzene (radical promoter) marketed by Peroxitalia Ltd;
CCDFB: 2.3 dimethyl-2,3-diphenyl butane (radical promoter) marketed by Peroxitalia Ltd.

All the flame retardant compositions prepared according to the process of the invention were tested in two ways preparing polymeric compounds: alone (without other synergists) in medium-high loaded compound (FR composition not less than 15% in weight) or in very low quantities in the presence of a radicals promoter. Table 1 shows how both solutions are effective even though the second proves preferable. When a certain proportion of ethylene (with Dutral CO054) is inserted the compound, a small extra amount of additive is sufficient to obtain good flame retardancy (FR) performance, even though it is known that the presence of ethylene disturbs the FR activity in this type of application.

TABLE 2

| | | | | |
|---|---|---|---|---|
| Edistir N1840 | 100 (comparative) | 98.5 | — | — |
| Pibiflex 2560 | — | — | 100 (comparative) | 98.5 |
| FR (example 1) | — | 1.25 | — | 1.25 |
| CCDFB | — | 0.25 | — | 0.25 |
| Oi | 18 | 22 | 17 | 21 |

TABLE 1

| | | | | | | | | | |
|---|---|---|---|---|---|---|---|---|---|
| PP moplen HF501N | 100 | 95 | 90 | 85 | 70 | 98.5 | 60 | 88 | 87 |
| Dutral CO054 | — | — | — | — | — | — | 10 | 10 | 10 |
| FR (Example1) | — | 5 | 10 | 15 | 30 | 1 | 30 | 1.5 | 2 |
| CCPIB | — | — | — | — | — | 0.5 | — | 0.5 | 1 |
| Oi | 18 | 20.5 | 21.5 | 24.5 | 25.5 | 32 | 25.5 | 25.5 | 24.5 |
| UL-94 | B | B | V-2 | V-2 | V-2 | V-2 | V-2 | V-2 | V-2 |
| Extinguishing times (s) | | 6; 20; B | 1; 1; 10 | 1; 1; 1 | 1; 1; 1 | 1; 1; 1 | 1; 1; 16 | 1; 1; 1 | 1; 1; 1 |

The data in Table 1 show that by adding only 5% of the flame retardant composition to the polymer of Example 1, the resulting compound shows "flame retardant" activity even though it did not pass the UL-VB test; an increase of approximately 2.5 index points of oxygen passing from the virgin matrix (col. 2) to the compound containing 5% of additive (col. 3) is in fact observed.

Table 2 shows how even a small amount of flame retardant composition from the process presented in example 1 in the presence of a radicals promoter makes it possible to achieve a good degree of flame resistance on the various polymer matrices tested.

TABLE 3

| | | | | | | | | | |
|---|---|---|---|---|---|---|---|---|---|
| FR (example 2) | 15 | — | — | — | 1.25 | — | — | — | — |
| FR (example 3) | — | 15 | — | — | — | 1.25 | — | — | — |
| FR (example 4) | — | — | 15 | — | — | — | 1.25 | — | — |
| FR (example 5) | — | — | — | 15 | — | — | — | — | 1.25 |
| CCPIB | — | — | — | — | 0.25 | 0.25 | 0.25 | 0.25 | 0.25 |
| Oi | 27 | 24.5 | 26.5 | 23 | 31.5 | 26.5 | 31 | 24.5 | 23 |
| UL-94 | V-2 | V-2 | V-2 | V-2 | V-2 | V-2 | V-2 | V-2 | — |
| Extinguishing times (s) | 1; 1; 1 | 1; 14; 1 | 1; 5; 1 | 1; 18; 10 | 1; 1; 2 | 1; 1; 1 | 1; 1; 1 | 1; 1; 1 | — |

TABLE 4

| | | | | | | | | | | |
|---|---|---|---|---|---|---|---|---|---|---|
| FR (example 6a) | 15 | — | — | — | — | 1.25 | — | — | — | — |
| FR (example 6b) | — | 15 | — | — | — | — | 1.25 | — | — | — |
| FR (example 6c) | — | — | 15 | — | — | — | — | 1.25 | — | — |
| FR (example 6c) | — | — | — | 15 | — | — | — | — | 1.25 | — |
| FR (example 6e) | — | — | — | — | 15 | — | — | — | — | 1.25 |
| CCPIB | — | — | — | — | — | 0.25 | 0.25 | 0.25 | 0.25 | 0.25 |
| Oi | 21 | 26 | 21 | 26 | 20 | 29 | 28 | 25 | 32 | 30.5 |
| UL-94 | V-2 | V-2 | V-2 | V-2 | B | V-2 | V-2 | V-2 | V-2 | V-2 |
| Extinguishing times (s) | 1; 3; 6 | 25; 1; 1 | 5; 1; 1 | 1; 5; 1 | — | 1; 1; 1 | 1; 1; 1 | 1; 1; 1 | 1; 1; 1 | 1; 1; 1 |

Tables 3 and 4 show the excellent level of "flame retardant" efficacy of the compositions prepared according to the process of the invention (examples 2 to 6)

TABLE 5

| | comparison 1 | | | | comparison 2 | | | |
|---|---|---|---|---|---|---|---|---|
| PP moplen HF501N | Complement to 100 net of stabilisers | | | | | | | |
| FR (example 1) | — | 1 | — | — | — | 0.6 | — | — |
| FR (example 4) | — | — | 1.25 | — | — | — | 0.6 | — |
| FR (example 6d) | — | — | — | 1.25 | — | — | — | 0.6 |
| ML/BiBr₃ complex | — | — | — | — | 0.5 | — | — | — |
| Melamine bromohydrate | 1.5 | — | — | — | — | — | — | — |
| Bismuth subcarbonate | 0.2 | — | — | — | — | — | — | — |
| CCPIB | 0.2 | 0.5 | 0.25 | 0.25 | 0.3 | 0.15 | 0.15 | 0.15 |
| Oi | 31.5 | 32 | 31 | 32 | 29.5 | 29 | 29 | 29.5 |
| UL-94 | V-2 | V-2 | V-2 | V-2 | V-2 | V-2 | V-2 | V-2 |
| Total package FR additives | 1.90% | 1.50% | 1.50% | 1.50% | 0.80% | 0.75% | 0.75% | 0.75% |

Table 5 shows the FR activity of some of the flame retardant compositions obtained according to the process of the invention, compared with two comparative compositions reported in the state of the art. In particular, solely by way of comparison, formulations were considered comprising only one of the two types of bromine present in the formulation of the invention, suitably formulated. The comparative composition 1 comprises only melamine bromohydrate without the complex, while the comparative composition 2 comprises only the ML/BiBr3 complex without melamine bromohydrate.

In the case in point, apart from the flame retardant effectiveness substantially similar or slightly higher in some cases, the flame retardant compositions obtained according to the process of the invention show excellent FR activity even when they are simply added to the polymer in the presence of the radicals promoter (CCPIB), while many of the FR compositions of the prior art require the addition of other synergists.

The invention permits numerous advantages to be achieved, in part already described.

The preparation process of a flame retardant composition made from halogenated bismuth and/or antimony compounds complexed with melamine according to the invention is applicable industrially more simply than the current processes.

In particular, the process according to the invention is more easily controllable to avoid degradation of the active compounds, without the need for direct control of the exothermy of the reactions.

Thanks to the presence of a reaction carrier which is not involved in the reactions and acts as a support for said reactions, the process according to the invention makes it possible to easily control the aggressiveness of the reagents, intermediates and reaction products. This has a positive effect on the life of the plant.

The process according to the invention makes it possible to prepare flame retardant compositions containing complexes of melamine and bromides of antimony or bismuth, avoiding the handling—outside the reactor—of metal bromides, unstable and dangerous substances.

The process according to the invention makes it possible to obtain a flame retardant composition made from brominated compounds of bismuth and/or of antimony complexed with melamine in a pure form, free of polymeric matrices, and thus utilisable as a general purpose active principle.

The process according to the invention makes it possible to obtain flame retardant compositions made from brominated compounds of bismuth and/or of antimony complexed with melamine with properties of chemical stability and limited aggressiveness, and thus easier to manipulate.

The invention thus conceived thereby achieves the intended objectives.

Obviously, its practical embodiments may assume forms and configurations different from those described while remaining within the scope of protection of the invention.

The invention claimed is:

1. Preparation process of a flame retardant composition made from brominated bismuth and/or antimony compounds complexed with melamine, the preparation process following at least one of the following reaction schemes:

$$Bi_2CO_5 + 6HBr \rightarrow 2BiBr_3 + 3H_2O + CO_2$$

$$BiBr_3 + ML \rightarrow \text{complex } ML/BiBr_3$$

$$HBr + ML \rightarrow MHB \qquad (I)$$

or $$Sb_2O_3 + 6HBr \rightarrow 2SbBr_3 + 3H_2O$$

$$SbBr_3 + ML \rightarrow \text{complex } ML/SbBr_3$$

$$HBr + ML \rightarrow MHB \qquad (II)$$

where ML indicates melamine and MHB indicates melamine bromohydrate, the process comprising the following operating steps:
a) providing the reagents provided for according to one of said two reaction schemes: melamine; at least one between bismuth carbonate and antimony sesquioxide; and hydrobromic acid in an aqueous solution;
b) placing said reagents in contact with each other in a reactor so as to trigger said chemical reactions and obtain a complex of brominated bismuth or brominated antimony with melamine and melamine bromohydrate,
characterised in that it comprises a step c) of providing at least one reaction carrier defined by at least one compound selected from the group consisting of melamine, melamine phosphate, melamine polyphosphate, ammonium phosphate, ammonium polyphosphate, triphenyl phosphate, graphite, silica, lignin, coke and compounds containing triazine rings condensed or linked by —NH groups,
and in that the reagents provided in step a) are placed in contact in step b) in the presence of at least one compound provided in step c) which is not involved in said reactions, polymeric compounds not being introduced in the reactor in such quantities as to create a polymer matrix, said reagents being introduced into the reactor in amounts defined by the stoichiometric ratios according to at least one of said two reaction schemes, said reaction carrier being introduced into the reactor in an amount defined with respect to the total weight of the reagents so that it can perform a modulator function.

2. Process according to claim 1, wherein the reaction carrier, defined by a single compound or by two or more compounds, is introduced in an amount of not less than 8% in weight with respect to the total weight of the reagents.

3. Process according to claim 2, wherein the contact between the reagents in the presence of the reaction carrier takes place in two sub-steps:

b1) introducing into the reactor, the melamine, the reaction carrier and at least one between the bismuth carbonate and antimony sesquioxide under continuous stirring to form a mixture;
b2) adding to said mixture, under continuous stirring, the hydrobromic acid in aqueous solution so as to trigger said chemical reactions.

4. Process according to claim 3, wherein the melamine, the reaction carrier and at least one between the bismuth carbonate and antimony sesquioxide are introduced into the reactor in dry state, preferably in the form of powders.

5. Process according to claim 4, wherein before the addition of the hydrobromic acid, the mixture of melamine, of the reaction carrier and of at least one between the bismuth carbonate and antimony sesquioxide is preheated, preferably to a temperature between 60° C. and 90° C.

6. Process according to claim 4 or 5, wherein after having added all the hydrobromic acid, the reactor is heated to remove all the water present and fully dry the reaction products, thus obtaining a dry raw product, preferably the reactor being heated to a temperature between 100° C. and 140° C.

7. Process according to claim 6, wherein the dry raw product is subjected to a micronisation process, preferably said micronisation process is conducted to bring the particles of the solid raw product to have a mean particle size comprised between 5 μm-50 μm, more preferably, comprised between 20 μm-30 μm or between 5 μm-10 μm.

8. Process according to claim 4, wherein the hydrobromic acid in aqueous solution is added to the mixture following a controlled dosage, in order to keep the mass of reagents and reaction products always in a semi-dry form or in the form of a workable paste.

9. Process according to claim 3, wherein the melamine, the reaction carrier and at least one between the bismuth carbonate and antimony sesquioxide are introduced into the reactor together with water obtaining a suspension, preferably the water being present in an amount such as to ensure that after the addition of the hydrobromic acid, the reactions take place in solution.

10. Process according to claim 9, wherein the hydrobromic acid in aqueous solution is added to said suspension without external heating, obtaining a raw reaction product in aqueous suspension.

11. Process according to claim 10, wherein after having added all the hydrobromic acid, the raw reaction product in aqueous suspension is subjected to drying to obtain a dry raw product.

12. Process according to claim 11, wherein the drying is achieved by spray drying.

13. Process according to claim 1, wherein in step b) the reagents are placed in contact with each other in the presence of only one reaction carrier, preferably melamine, the total quantity of melamine being introduced into the reactor in excess of the stoichiometric amount in relation to the amount of the other reagents, preferably the melamine in excess being not less than 8% in weight of the reagents.

* * * * *

UNITED STATES PATENT AND TRADEMARK OFFICE
CERTIFICATE OF CORRECTION

PATENT NO. : 9,879,184 B2
APPLICATION NO. : 15/517355
DATED : January 30, 2018
INVENTOR(S) : Anita Castellucci et al.

It is certified that error appears in the above-identified patent and that said Letters Patent is hereby corrected as shown below:

Column 21, Claim 1, Line 11, after "$BiBr_3 + ML \rightarrow$ complex $ML/BiBr_3$" insert -- (I) --.

Column 21, Claim 1, Line 18, after "$SbBr_3 + ML \rightarrow$ complex $ML/SbBr_3$" insert -- (II) --.

Column 22, Claim 6, Line 17, after "claim 4" delete "or 5".

Signed and Sealed this
Third Day of July, 2018

Andrei Iancu
*Director of the United States Patent and Trademark Office*